United States Patent
Melton

(10) Patent No.: US 9,360,397 B1
(45) Date of Patent: Jun. 7, 2016

(54) ANCHOR INSPECTION DEVICE

(71) Applicant: William H Melton, LaVergne, TN (US)

(72) Inventor: William H Melton, LaVergne, TN (US)

(*) Notice: Subject to any disclaimer, the term of this patent is extended or adjusted under 35 U.S.C. 154(b) by 124 days.

(21) Appl. No.: 14/321,928

(22) Filed: Jul. 2, 2014

(51) Int. Cl.
*G01N 3/08* (2006.01)
*G01M 99/00* (2011.01)
*G01L 1/00* (2006.01)
*G01L 5/00* (2006.01)
*E02D 33/00* (2006.01)

(52) U.S. Cl.
CPC ............... *G01M 99/007* (2013.01); *G01L 1/00* (2013.01); *E02D 33/00* (2013.01); *G01L 5/0033* (2013.01); *G01N 3/08* (2013.01); *G01N 2203/0003* (2013.01); *G01N 2203/0017* (2013.01)

(58) Field of Classification Search
CPC ...................... G01L 5/0033; G01N 2203/0003; G01N 2203/0017; G01N 3/08; E02D 33/00
USPC .............. 73/761, 786, 826, 827, 828, 862.01, 73/862.381, 862.391–892.393, 862.542, 73/862.584
See application file for complete search history.

(56) References Cited

U.S. PATENT DOCUMENTS

| | | | | | |
|---|---|---|---|---|---|
| 3,738,163 | A * | 6/1973 | McEntire | .................. | G01N 3/10 73/761 |
| 3,942,368 | A * | 3/1976 | Hoyt | ..................... | G01L 5/0033 73/784 |
| 4,753,115 | A * | 6/1988 | Moody | ..................... | G01N 3/08 73/826 |
| 5,792,961 | A * | 8/1998 | Giebner | ..................... | G01N 3/08 73/786 |
| 7,175,368 | B2 * | 2/2007 | Stotzer | ..................... | E02D 33/00 405/232 |
| 7,441,471 | B1 * | 10/2008 | Davis | ....................... | E02D 7/22 405/303 |
| 7,513,168 | B2 * | 4/2009 | Alba | ........................ | G01N 3/16 73/818 |
| 8,402,837 | B1 * | 3/2013 | Jones | .................. | G01M 5/0058 73/788 |
| 2005/0074297 | A1 * | 4/2005 | Stoetzer | ................. | E02D 33/00 405/233 |

* cited by examiner

*Primary Examiner* — Lisa Caputo
*Assistant Examiner* — Jonathan Dunlap
(74) *Attorney, Agent, or Firm* — Lucian Wayne Beavers; Patterson Intellectual Property Law, PC

(57) ABSTRACT

An anchor testing device is configured to operate with a load cell sensor and is designed to apply a force through a load cell sensor to an anchor it is testing. The anchor testing device can comprise a top support having a generally centrally located sensor attachment location and three stanchions with each stanchion suspending from a top support and being spaced from the adjacent stanchions. The stanchions can be configured in a generally triangular shape. The device can further comprise a bottom support operatively attached to each stanchion wherein the bottom support and top supports are positioned to maintain the spacing between adjacent stanchions. The device can comprise a load cell sensor support that is positioned below the top support and is operatively attached to the top support or the bottom support. The load cell sensor support is shaped and positioned to engage the load cell sensor and restrict movement of the load cell sensor when the load cell sensor is used with the anchor testing device.

23 Claims, 9 Drawing Sheets

ANCHOR INSPECTION DEVICE

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

All patents and publications described or discussed herein are hereby incorporated by reference in their entirety.

BACKGROUND OF THE DISCLOSURE

The present disclosure relates generally to post-installed anchor testing and a device to accomplish that testing.

More particularly, but not by way of limitation, the present disclosure relates to a device and kit used to check the strength of anchors used for buildings and in the construction processes.

BACKGROUND OF THE ART

The construction industry gives a lot of attention to the materials and structure used in erecting a building. There are numerous building codes and safety requirements in virtually every jurisdiction in the United States. These codes are designed to insure a level of safety, for both the materials used and the construction process using those materials, when erecting the building/structure.

One area in particular in which the building codes require testing is to the anchors that secure the building to the ground or the building's components to the foundation of that building. These anchors typically are large threaded rods used to secure aspects of the building to the foundation, such as large equipment and/or walls and beams that could eventually support portions of the building itself. Obviously, if these anchors are not properly installed the equipment could malfunction and/or the building could not withstand the environment and elements around it. This could ultimately lead to a collapse in that structure. As such, these anchors need to be tested to insure that the anchors will perform as engineered and function properly under the stresses of the constructed building.

Further complicating this effort is the fact that these anchors are not always positioned in readily accessible locations. For example, the anchors could have various structures around them or above them that restricts the space immediately above and/or restricts a portion of the area around that anchor. This fact can cause a serious issue when testing those anchors. If a technician is unable to properly access the anchor, a proper test can obviously not occur.

What is needed therefore is an anchor testing device and kit that allows a technician to access a variety of anchors in order to properly test those anchors to comply with building codes and/or any safety or construction requirements. This needed anchor testing device and kit is lacking in the art.

BRIEF SUMMARY OF THE DISCLOSURE

The present disclosure provides an anchor testing device and kit for the testing of anchors after those anchors are installed at a construction site. This device and kit overcomes the drawbacks and limitations of the prior art.

The anchor testing device is configured to operate with a load cell sensor and is designed to apply a force through the load cell sensor to the anchor it is testing. The anchor testing device can comprise a top support having a generally centrally located sensor attachment location. The device can further comprise three stanchions with each stanchion suspending from a top support and being spaced from the adjacent stanchions. The stanchions can be configured in a generally triangular shape. The device can further comprise a bottom support operatively attached to each stanchion wherein the bottom support and top supports are positioned to maintain the spacing between adjacent stanchions. Further, the device can comprise a load cell sensor support that is positioned below the top support and is operatively attached to the top support or the bottom support. The load cell sensor support is shaped and positioned to engage the load cell sensor and restrict movement of the load cell sensor when the load cell sensor is used with the anchor testing device.

Each stanchion can include a leveling device and an extension. The extension can be positioned opposite the top support and shaped to vary the length of a stanchion. The stanchions can include a threaded portion to facilitate this movement.

The top support can be triangularly shaped and the sensor attachment location in the top support can be positioned within the generally triangular shape of the stanchions and/or top plate. Further, the bottom support can be triangularly shaped and can be positioned adjacent to the top support or spaced from the top support. The sensor attachment location is preferably shaped and positioned to accept a force through the load cell sensor when a load cell sensor is used with the anchor testing device.

Also included is an anchor testing kit for testing installed anchors. The kit comprises a load cell sensor, a load display, a force conduit, an anchor connection, and an anchor testing device. When assembled the load cell sensor will have a first and a second end with the force conduit operatively connected to the first end of the load cell sensor. The anchor connection can be operatively connected to the second end of the load cell sensor. The force conduit can be attached to the centrally located sensor attachment location while the anchor connection can be positioned to engage and secure the anchor testing device to the anchor being tested. The load display can be operatively connected to the load cell sensor to indicate the amount of force used during the testing of the anchor.

It is therefore a general object of the current disclosure to provide an anchor testing kit.

Another object of the current disclosure is to provide an anchor testing device used to test installed anchors in the construction process.

Still another object of the current disclosure is to provide an anchor testing device that allows a technician or a user more access to various anchors used in the construction process and to allow ease of access to those anchors for building code, structural, and safety testing.

Other and further objects, features, and advantages of the present disclosure will be readily apparent to those skilled in the art upon reading of the following disclosure when taken in conjunction with the accompanying drawings.

BRIEF DESCRIPTION OF THE SEVERAL VIEWS OF THE DRAWINGS

The accompanying drawings are incorporated and constitute part of the specification. The drawings illustrate optional embodiments of the apparatus and, together with the descriptions, serve to explain some principles of the apparatus.

DETAILED DESCRIPTION OF THE INVENTION

Figure 1:
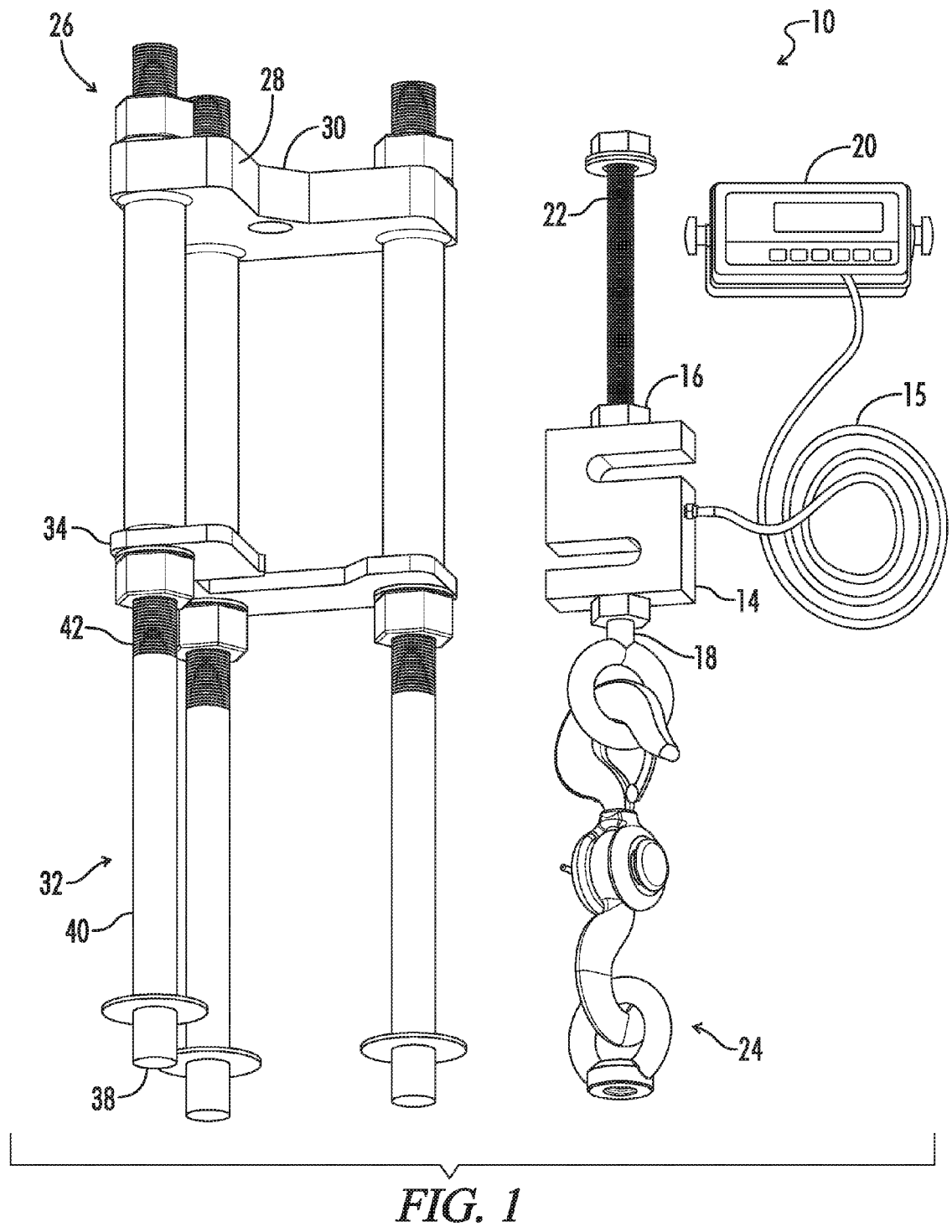
FIG. 1 shows an exploded view of an anchor testing kit made in accordance to the current disclosure.

Referring generally now to FIGS. 1-13, an anchor testing kit is shown and generally designated by the numeral 10. The kit is for testing installed anchors 12 that are used in the building and construction process, especially those anchors 12 that are proximate to objects, such as posts, walls, etc., that limit access to the anchor 12 to be tested. The kit comprises a load cell sensor 14 having a first end 16 and a second end 18. A load display 20 is operatively connected to the load cell sensor 14, while a force conduit 22 is operatively connected to the first end 16 of the load cell sensor 14. An anchor connection 24 is operatively connected to the second end 18 of the load cell sensor 14.

The kit 10 further comprises an anchor testing device 26 and stanchions 32. The anchor testing device 26 is a portable device that is designed for ease of movement by preferably a single technician. The anchor testing device 26 includes a top support 28, which can be alternately described as a top plate 28, having a generally centrally located sensor attachment location 30. The stanchions 32, preferably three in number, extend from the top support 28 and are spaced from adjacent stanchions. The stanchions 32 are configured in a generally triangular shape. A bottom support 34, which can be alternately described as a bottom plate 34, is operatively attached to each stanchion 32 with the bottom support 34 and top support 28 positioned to maintain the spacing between the adjacent stanchions 32. The stanchions 32 can be attached to the top support and/or bottom support by a fastener 46, such as a nut or threaded connection. A load cell sensor support 36 is positioned below the top support 28 and is operatively attached to the top support 28 or the bottom support 34. The load cell sensor support 36 is shaped and positioned to engage the load cell sensor 14 and restrict movement of the load cell sensor 14 when used with the anchor testing device 28.

Figure 4:
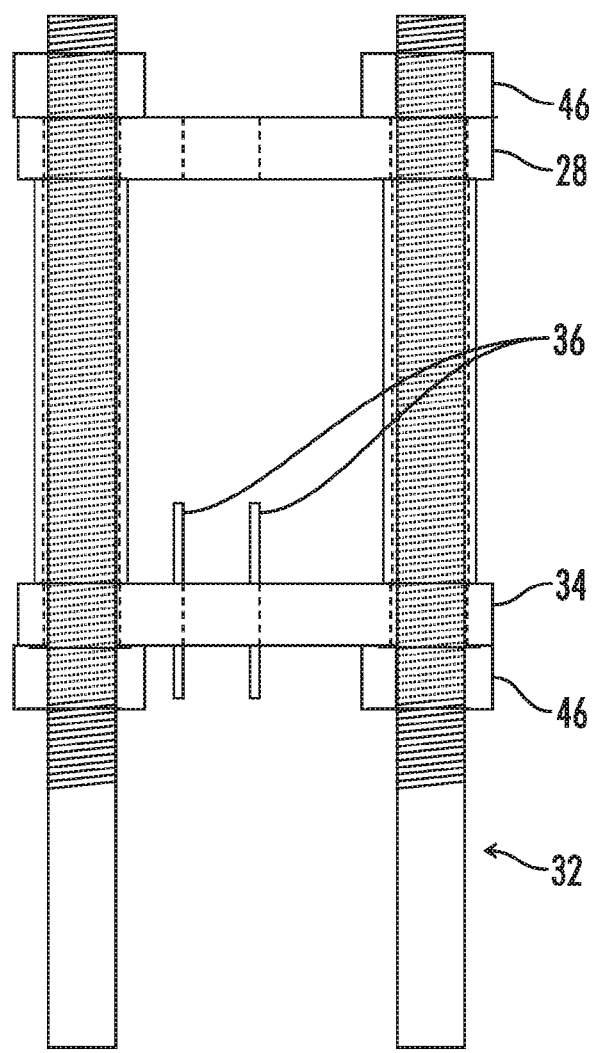
FIG. 4 is a side view of the anchor testing device shown in FIGS. 1 and 2.
Figure 5:
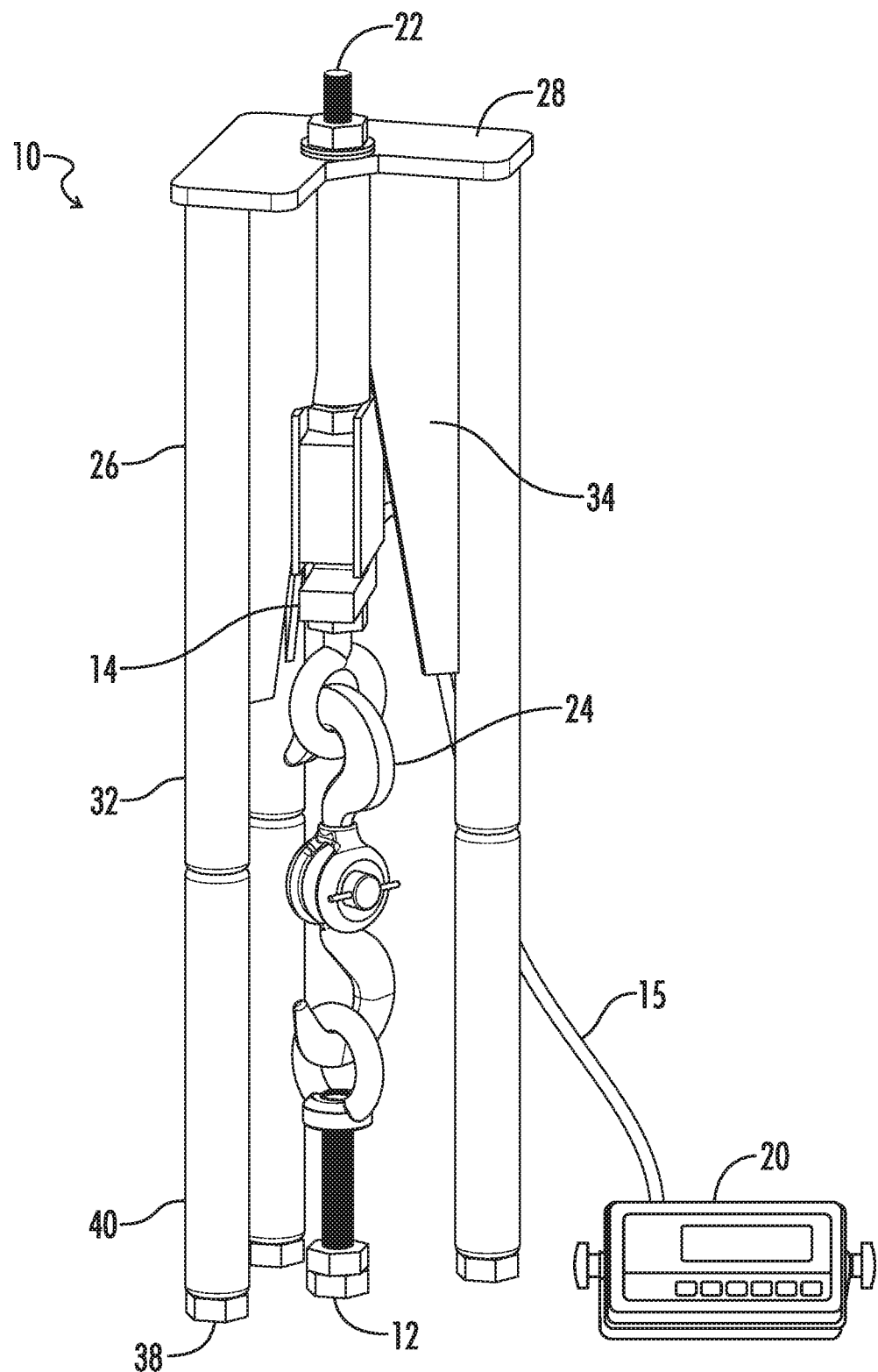
FIG. 5 is a perspective view of an alternative embodiment of an anchor testing kit made in accordance with the current disclosure.

In preferred embodiments, the anchor testing device 26 can have one or more additional features. For example, the stanchions 32 can include a leveling device 38 used to facilitate positioning of the stanchions 32 around the anchors 12 that are to be tested. The leveling device 38 can be the type of leveling devices known in the art, including threaded leveling devices. The leveling device 38 on the stanchions allows the anchor testing device 26, and the anchor testing kit 10, to adapt to contours in the surrounding areas of the anchors 12. Additionally, each stanchion 32 can include an extension 40 that is positioned opposite the top support 28. The extension 40 can be shaped to vary the length of the stanchion 32 to which it is attached. The extensions 40 can be used to vary the height of the anchor testing device 26 to allow the anchor testing kit 10 to adapt to test anchors 12 in multiple environments. As such, the anchor testing kit 10 can still test anchors 12 that have a low height clearance above them by adjusting the extensions 40 on the stanchions 32. The extensions 40 can include a threaded portion 42. The extensions 40 can be additional legs or posts added to the stanchions 32, as best seen in FIG. 5. Alternately, the extensions 40 can be threaded posts as illustrated in FIG. 4. The extensions 40 in combination with the leveling device 38 allow a technician that uses the anchor testing kit 10 and the anchor testing device 26 to adapt the anchor testing device 26 and the kit 10 to most environments in which anchors 12 are placed and are in need of testing.

Figure 2:
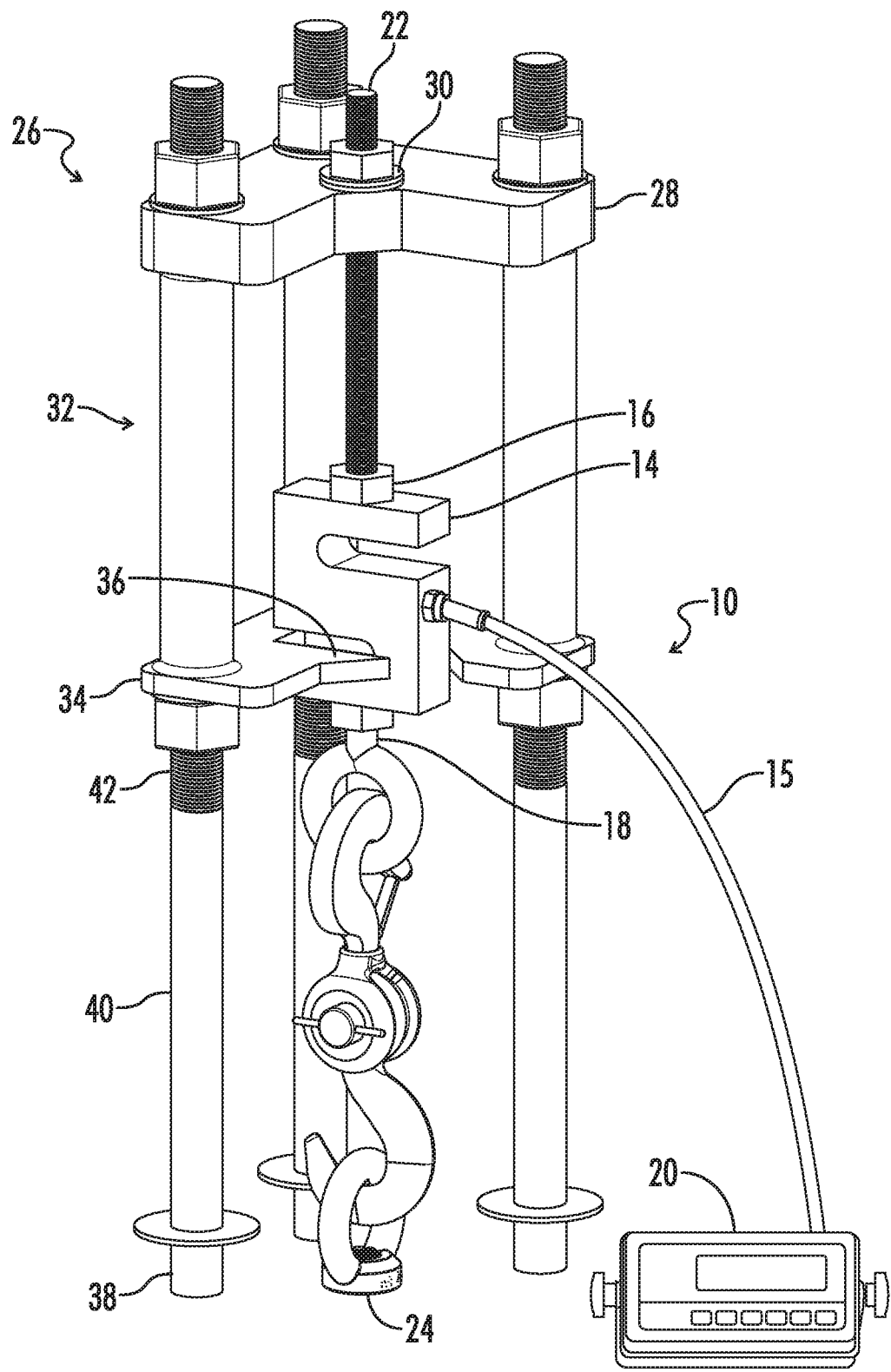
FIG. 2 is a perspective view of an embodiment of an assembled anchor testing kit.
Figure 3:
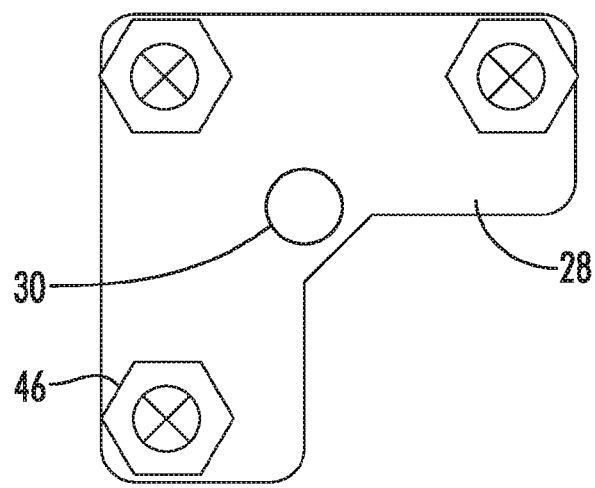
FIG. 3 is a top view of the anchor testing device shown in FIGS. 1 and 2.
Figure 6:
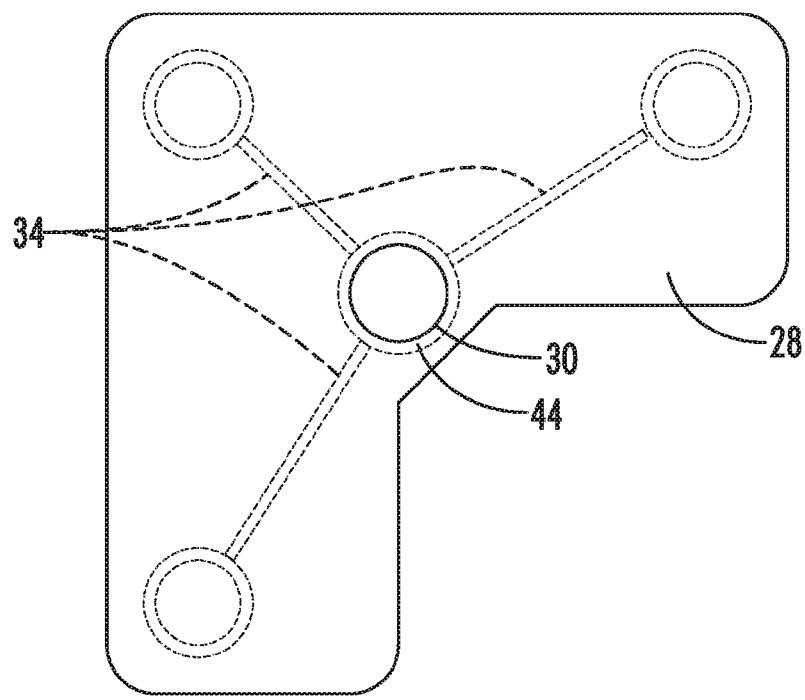
FIG. 6 is a top view of the anchor testing device shown in FIG. 5.
Figure 7:
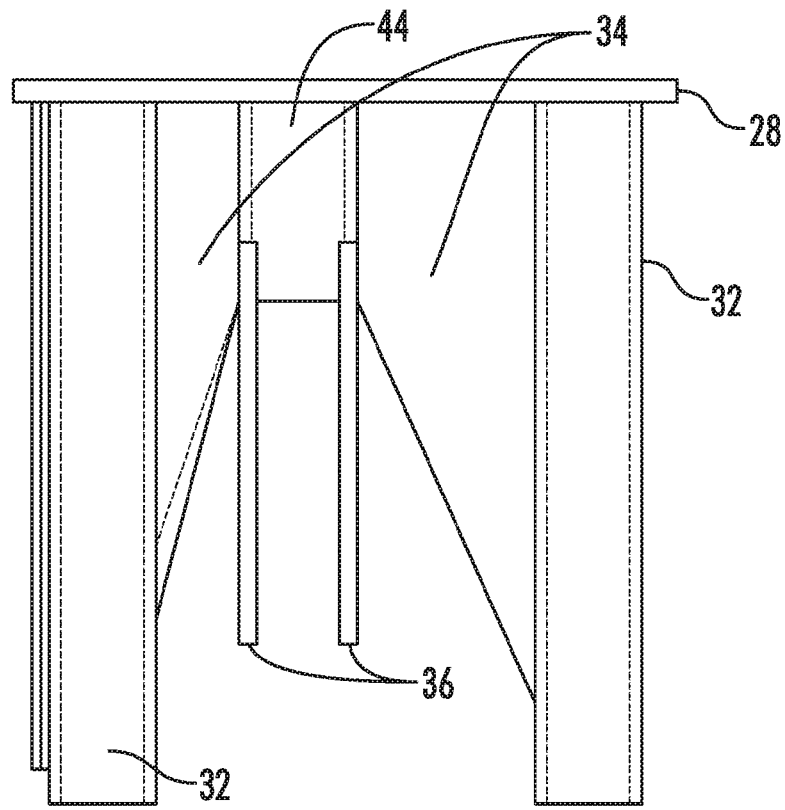
FIG. 7 is a side view of the anchor testing device shown in FIG. 5.
Figure 9:
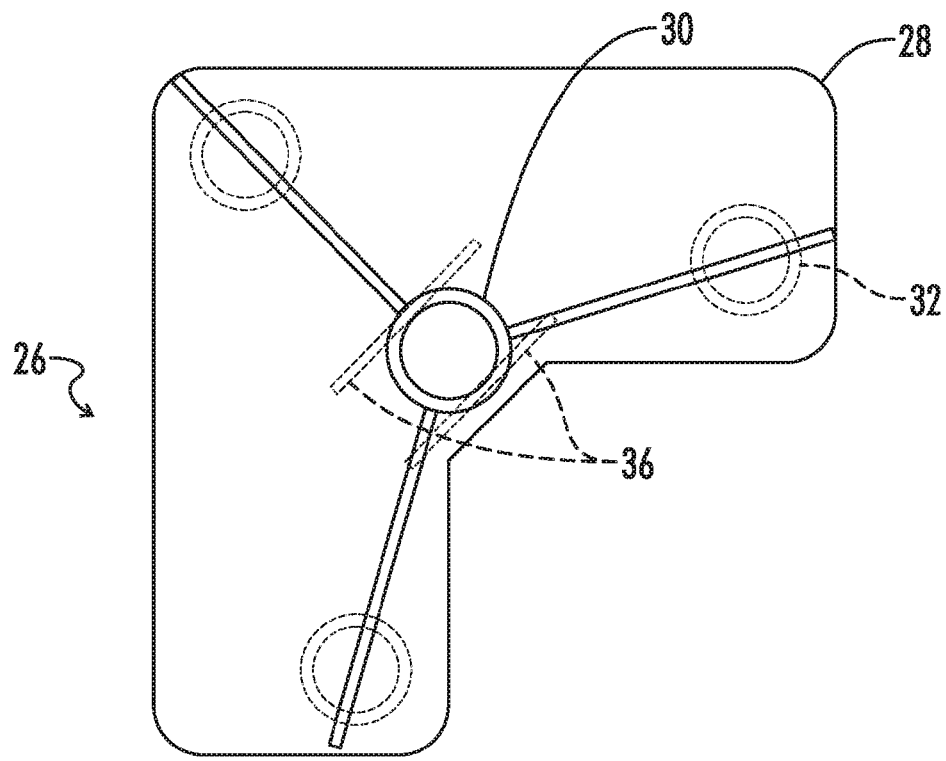
FIG. 9 is a top view of the anchor testing device shown in FIG. 8.

The sensor attachment location 30 of the anchor testing device 26 is preferably positioned within the generally triangular shape of the stanchions 32. This facilitates a better force distribution through the stanchions 32 when testing the anchors 12. Additionally, the top support 28 and/or the bottom support 34 can be triangularly shaped. This is best illustrated in FIGS. 3, 6 and 9. In an embodiment, the sensor attachment location 30 can be positioned within the triangular shaped footprint of both the top support 28 and the bottom support 34. In an embodiment, the bottom support can be positioned spaced from the top support 28 as illustrated in FIGS. 1, 2 and 4. Alternatively, the bottom support 34 can be positioned adjacent to the top support 28 as illustrated in FIGS. 5 and 7.

In an embodiment of the anchor testing device 26, the load cell sensor support 36 can be part of the bottom support 34 as illustrated in FIGS. 1, 2 and 4. In these embodiments, the load cell sensor support 36 is shaped to accept the load cell sensor 14. The support 36 restricts movement of the sensor 14 when the sensor 14 experiences the load placed upon it during the testing of the anchors 12 by the kit 10. The support 36 can also extend from the top support 28 or the bottom support 34.

Figure 8:
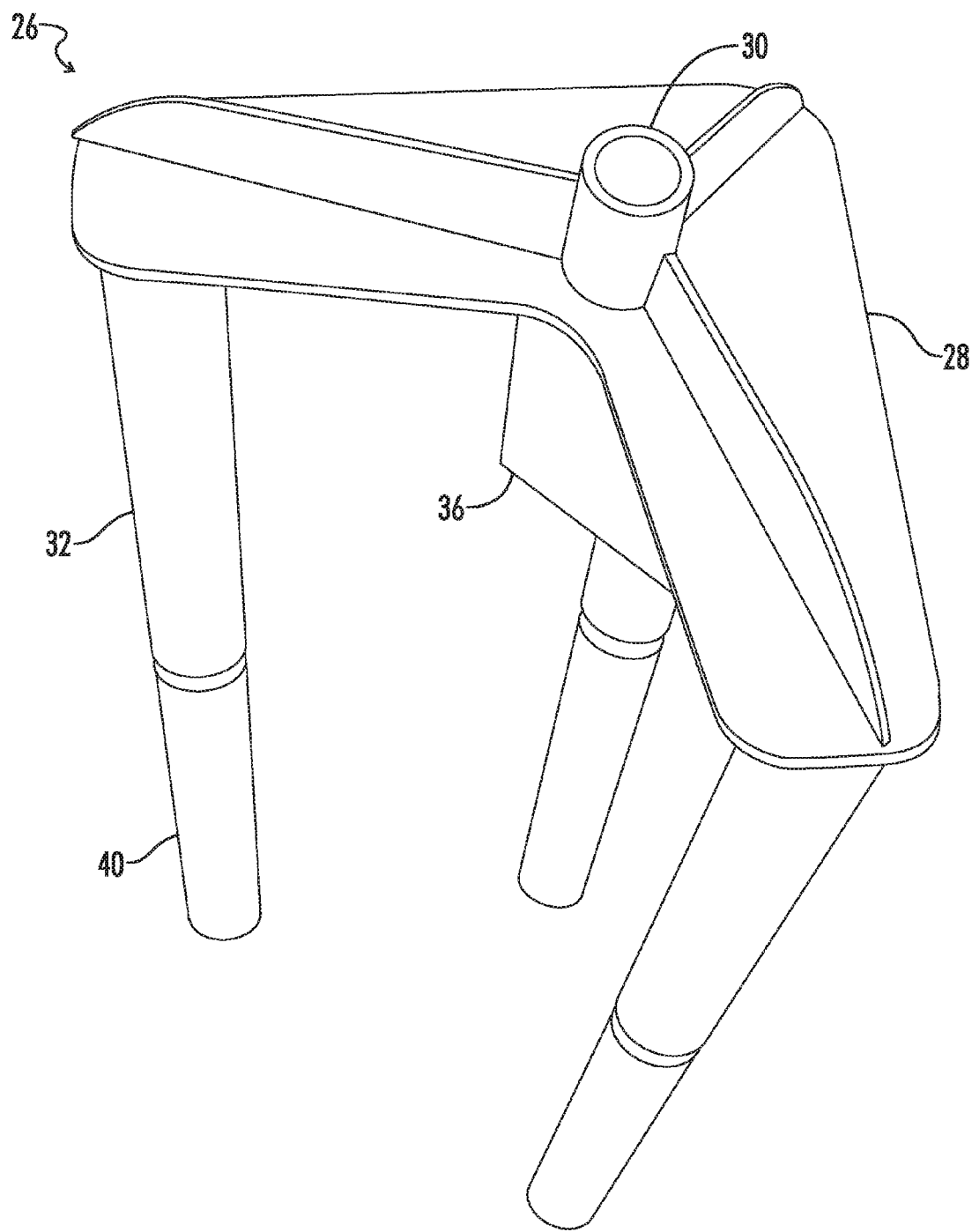
FIG. 8 is a top perspective view of another alternative embodiment of an anchor testing device.
Figure 10:
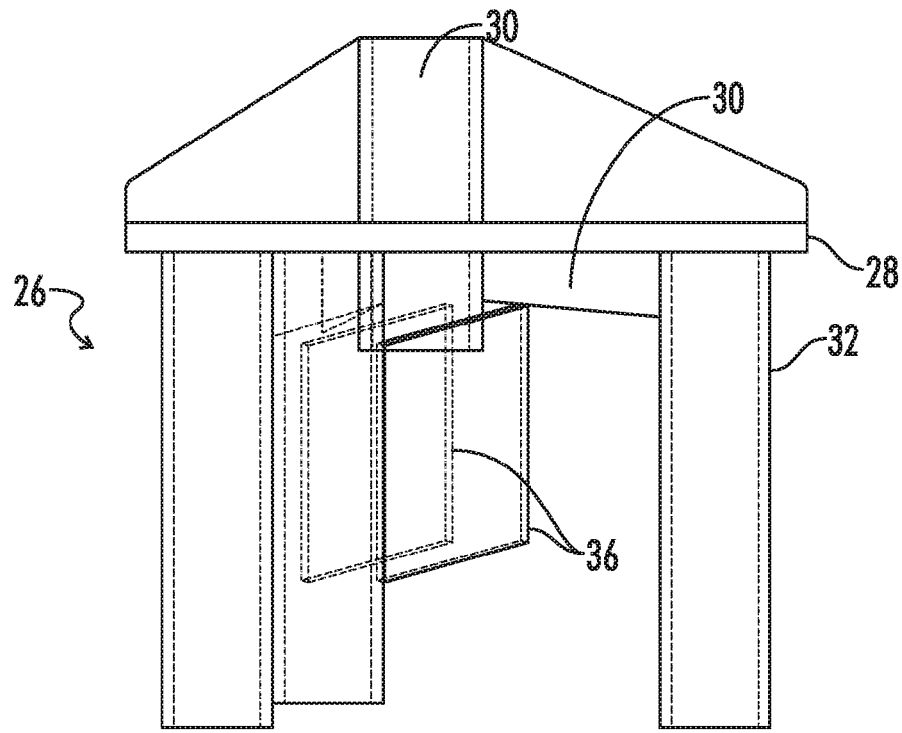
FIG. 10 is a side view of the anchor testing device shown in FIG. 8.

In an embodiment as seen in FIGS. 1, 2 and 4, the bottom support 34 can be a generally horizontal plate engaging the stanchions 32. In another embodiment, the bottom support 34 can be various plates extending generally parallel with the stanchions 32 and extending over to a center support 44 as shown in FIGS. 5 and 7. This center support 44 can accept the force conduit 22 as shown in these figures. In yet another embodiment, the bottom support can be a hybrid design that includes some of the horizontal and generally parallel features of the previously described bottom supports 34. This is best shown in FIGS. 8-10.

Figure 11:
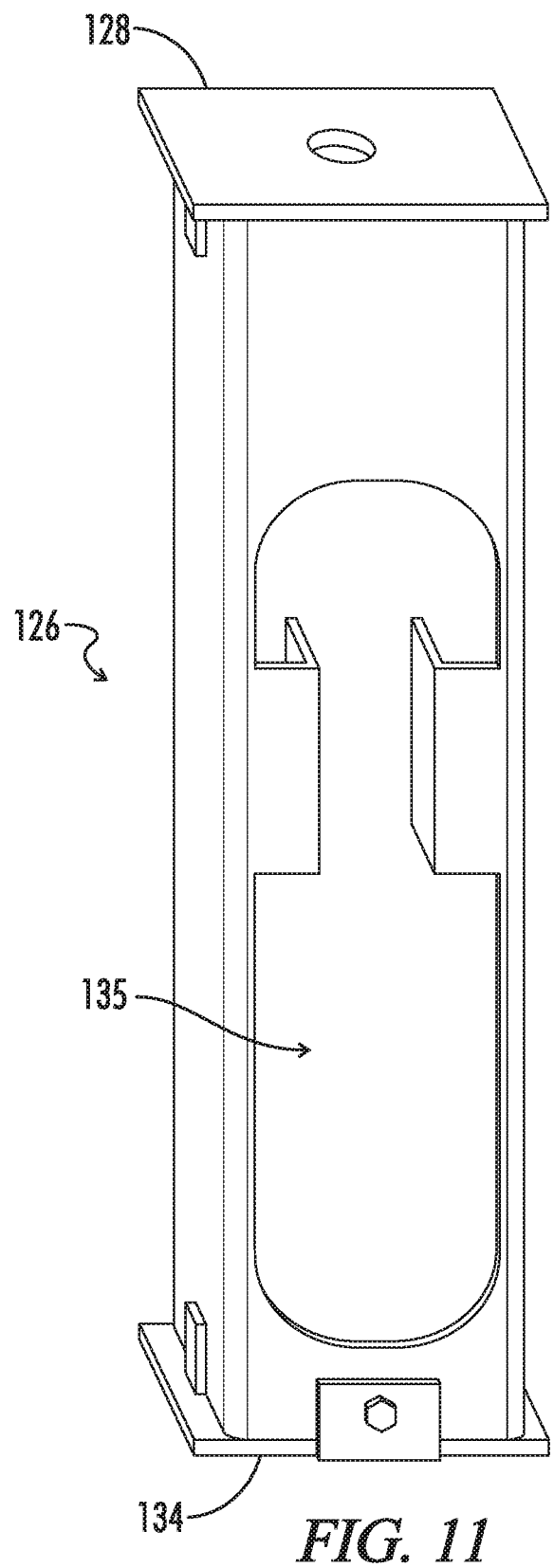
FIG. 11 is a perspective view of another alternative embodiment of an anchor testing device.
Figure 12:
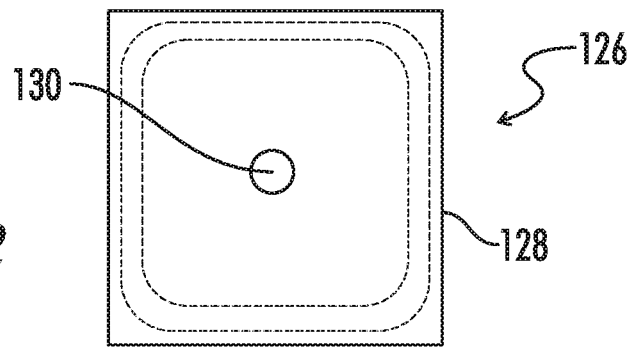
FIG. 12 is a top view of the anchor testing device shown in FIG. 11.
Figure 13:
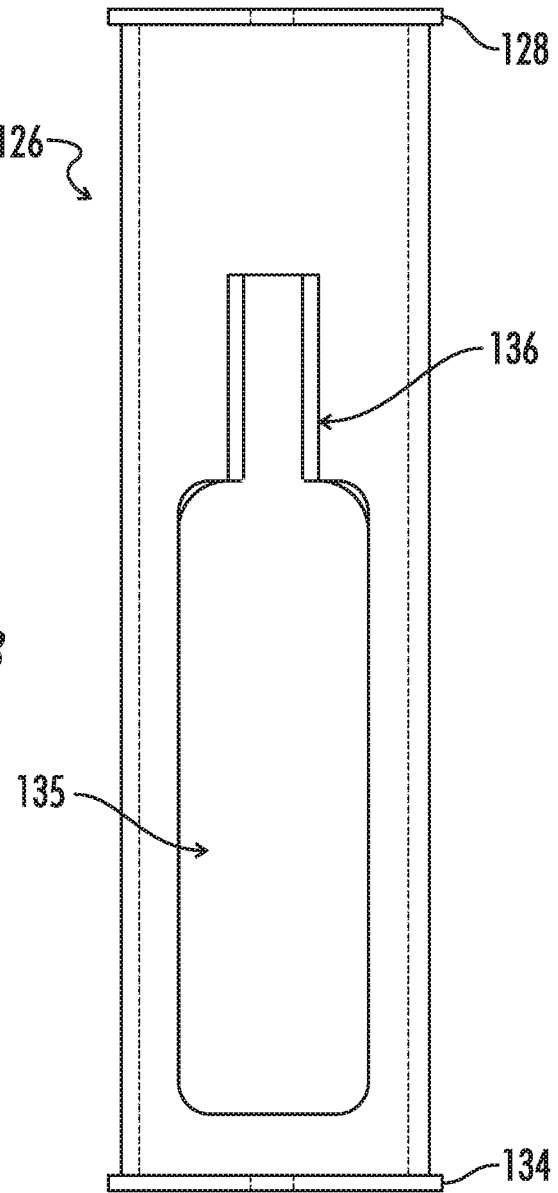
FIG. 13 is a side view of the anchor testing device shown in FIG. 11.

In another embodiment as seen in FIGS. 11-13, the anchor testing device is an anchor testing device 126. This anchor testing device 126 generally has a four sided configuration having an internal cavity 135 that accepts the load sensor 14, force conduit 22 and anchor connection 24. The anchor testing device 126 can include top and bottom plates 128 and 134, respectively, which provide stability and alignment for the anchor testing device 126 and the load cell sensor 14, the force conduit 22 and anchor connections 24. The anchor testing device 126 can include a load cell sensor support 136, such as a narrowed opening or slot near the opening to the cavity 135. This is best shown in FIGS. 11-13.

In an embodiment, the anchor testing kit 10 can be assembled as shown in FIG. 2. When assembled, the kit 10 is designed to test an anchor 12 that is being used in the building or construction process.

In operation, the kit 10 can be utilized as follows. The anchor testing device 26 can be located approximate to an anchor 12, preferably by a single technician due to the portable nature of the design. The force conduit 22, such as a rod 22, can be attached to the sensor attachment location 30, which can be an opening in the top support 28. The force conduit 22 can extend from the sensor attachment location 30 to the load cell sensor 14 and attach to the first end 16 of the sensor 14. The second end 18 of the sensor 14 can attach to an anchor connection 24. This anchor connection can have various fasteners, as known in the art, to attach to an anchor 12. The anchor connector 24 can preferably be threaded to accept the threaded end of standard anchors 12.

An information conduit 15, such as a wired or wireless connection, can operatively connect the sensor 14 and the load display 20. The load display 20, which can be a digital indicator, provides an indication of the load being applied to the anchor 12 during the testing process. The load display 20 and the load cell sensor 14 can be integrated operatively into a single unit without necessarily the need for the information conduit 15.

Once assembled, a technician can adjust the force conduit 22 to apply a force through the load sensor 14 to the anchor 12. For example, a technician can adjust a threaded portion of the force conduit 22 such that the force conduit 22 pulls on the load sensor 14, which in turn pulls on the anchor connection 24, which in turn pulls on the anchor 12. The force conduit 22 can utilize a fastener, such as a nut, to translate the force conduit 22 upward away from the anchor 12. This motion uses the anchor testing device 26 as a base from which to exert the force onto the anchor 12.

The anchor testing kit 10 can be described as a pull test jig type testing kit. The kit 10 can be preferably supported at three points of contact with a foundation or ground surrounding the anchor 12 and have versatile adjustment capability in the leveling device 38 and extensions 40. This kit 10 and anchor testing device 26 will allow for force testing, or pull testing, of numerous items and various anchor types. These anchor types can include post installed epoxy and mechanical anchors that could be in concrete, masonry, wood, plastics and other materials. The kit 10 can also test lightweight welded attachments and epoxy attachments that have been utilized on virtually any surface.

The triangle stanchions 32 design allows for versatility in load applications and placement of the anchor testing device 26 when testing the anchors. For example, this design allows for testing in restricted areas wherein access to the anchor 12 can be limited by an object. The anchor testing device 26 can be modified to accept the various types of load cell sensors and the top support 28 and bottom supports 34 can be modified to allow for these various sensors 14 and the location of anchors 12.

In an embodiment, the anchor testing kit 10, and specifically anchor testing device 26 can be light weight enough for a single technician to operate. In alternate embodiments, the anchor testing device 26 can be adapted for automation or heavy loading applications as desired.

The loads that travel through the force conduit 22 and the load sensor 14 to the anchor connection 24 and anchor 12 can be applied through rotational torque, as can be realized with a nut and thread arrangement between the force conduit and a fastener. In an embodiment, this force application has been tested to 8 kps. In one testing experiment, the load cell sensor was a S-beam NTEP 10,000 Class III L Load Cell while the load display was a TI 500E Plus Digital Weight Indicator. With this kit 10, the anchors can be loaded to a point exceeding any load requirements for the construction applications in which they are used and maintain that load for any period of time as required by any governing body, such local, state, and federal building code and safety requirements.

Thus, although there have been described particular embodiments of the present invention of a new and useful Anchor Inspection Device it is not intended that such references be construed as limitations upon the scope of this invention except as set forth in the following claims.

What is claimed is:

1. An anchor testing device configured to operate with a load cell sensor to test installed anchors, the anchor testing device comprising:
   a top support having a generally centrally located sensor attachment location;
   three stanchions, each stanchion extending from the top support and spaced from the adjacent stanchions, the stanchions configured in a generally triangular shape;
   a bottom support, each stanchion being connected to the bottom support, the bottom support and top support positioned to maintain the spacing between adjacent stanchions; and
   a load cell sensor support positioned below the top support and operatively attached to the top support or the bottom support, the load cell sensor support shaped and positioned to engage the load cell sensor and restrict rotational movement of the load cell sensor when the load cell sensor is used with the anchor testing device.

2. The anchor testing device of claim 1, wherein each stanchion includes a leveling device.

3. The anchor testing device of claim 1, wherein each stanchion includes an extension positioned opposite the top support, the extension shaped to vary the length of the stanchion.

4. The anchor testing device of claim 3, wherein each extension includes a threaded portion.

5. The anchor testing device of claim 1, wherein the sensor attachment location in the top support is positioned within the generally triangular shape of the stanchions.

6. The anchor testing device of claim 1, wherein the top support is triangularly shaped.

7. The anchor testing device of claim 1, wherein the bottom support is triangularly shaped.

8. The anchor testing device of claim 1, wherein the bottom support is positioned adjacent to the top support.

9. The anchor testing device of claim 1, wherein the bottom support is spaced from the top support.

10. The anchor testing device of claim 1, wherein the sensor attachment location is shaped to accept a force through the load cell sensor when the load cell sensor is used with the anchor testing device.

11. The anchor testing device of claim 1, wherein the three stanchions extend parallel to each other.

12. The anchor testing device of claim 1, wherein the device includes three and only three stanchions.

13. The anchor testing device of claim 1, further comprising:
   a rod having a threaded upper end portion extending through the sensor attachment location of the top support and having a rod lower end;
   a nut engaging the threaded upper end portion of the rod above the top support;

a load cell sensor having an upper load cell end and a lower load cell end, the upper load cell end being connected to the rod lower end;

an anchor connector connected to lower load cell end, the anchor connector being configured to connect the load cell to an anchor to be tested; and wherein the load cell sensor support is configured to prevent rotation of the load cell sensor when the nut is rotated relative to the rod to apply a tension load to the anchor to test the anchor.

14. An anchor testing device, comprising:

first, second and third parallel stanchions, each stanchion including an extendible lower end for adjusting a length of each respective stanchion, the first, second and third stanchions defining the corners of an inner triangular area when viewed in a direction parallel to the lengths of the stanchions; and a support assembly connected to the stanchions and configured to maintain the stanchions parallel to each other when a compressive load is applied to the stanchions through the support assembly, the support assembly including a sensor attachment location located within the inner triangular area defined by the first, second and third stanchions.

15. The anchor testing device of claim 14, further comprising:

a rod having a threaded upper end portion extending through the sensor attachment location of the support assembly and having a rod lower end;

a nut engaging the threaded upper end portion of the rod above the support assembly;

a load cell sensor having an upper load cell end and a lower load cell end, the upper load cell end being connected to the rod lower end;

an anchor connector connected to lower load cell end, the anchor connector being configured to connect the load cell to an anchor to be tested; and a load cell sensor support connected to the support assembly and configured to prevent rotation of the load cell sensor when the nut is rotated relative to the rod to apply a tension load to the anchor to test the anchor.

16. The anchor testing device of claim 14, wherein the support assembly comprises:

an upper support plate;

a lower support plate; and first, second and third support tubes extending between the upper and lower support plates.

17. The anchor testing device of claim 16, wherein:

the first, second and third stanchions each include a threaded stanchion rod extending through the first, second and third support tubes, respectively, and each stanchion includes an upper nut threadedly engaging an upper portion of the respective stanchion rod above the upper support plate and a lower nut threadedly engaging a lower portion of the respective stanchion rod below the lower support plate, so that each stanchion rod is adjustably positioned relative to the support assembly.

18. The anchor testing device of claim 17, wherein:

the sensor attachment location is defined on the upper support plate; and the lower support plate includes a load cell sensor support configured to prevent rotation of a load cell sensor when a tension load is applied to an anchor to test the anchor.

19. The anchor testing device of claim 14, wherein the support assembly comprises:

an upper support plate;

first, second and third support tubes extending downward from the upper support plate; and first, second and third gusset plates extending between the first, second and third support tubes, respectively, and the upper support plate.

20. The anchor testing device of claim 19, wherein:

the sensor attachment location is defined on the upper support plate; and the support assembly further includes a load cell sensor support configured to prevent rotation of a load cell sensor when a tension load is applied to an anchor to test the anchor.

21. The anchor testing device of claim 14, wherein the support assembly comprises:

an upper support plate;

first, second and third stanchion support tubes extending downward from the upper support plate;

a central sensor support tube extending upward from the upper support plate, the central sensor support tube defining the sensor attachment location therethrough; and a plurality of upper gusset plates extending between an upper side of the upper support plate and the central sensor support tube.

22. The anchor testing device of claim 14, wherein the device includes three and only three stanchions.

23. The anchor testing device of claim 14, wherein the extendible lower end for adjusting a length of each respective stanchion allows the device to be leveled to adapt to contours in an area surrounding and anchor to be tested.

* * * * *